US009408951B2

(12) United States Patent
Larsen et al.

(10) Patent No.: US 9,408,951 B2
(45) Date of Patent: Aug. 9, 2016

(54) NANOPARTICLE IMPLANTATION IN MEDICAL DEVICES

(71) Applicant: Boston Scientific Scimed, Inc., Maple Grove, MN (US)

(72) Inventors: Steven R. Larsen, Lino Lakes, MN (US); Eric Petersen, Maple Grove, MN (US); Scott R. Schewe, Eden Prairie, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 156 days.

(21) Appl. No.: 14/078,167

(22) Filed: Nov. 12, 2013

(65) Prior Publication Data
US 2014/0134322 A1 May 15, 2014

Related U.S. Application Data

(60) Provisional application No. 61/725,581, filed on Nov. 13, 2012.

(51) Int. Cl.
*A61L 31/14* (2006.01)
*A61L 29/10* (2006.01)
(Continued)

(52) U.S. Cl.
CPC ............... *A61L 31/14* (2013.01); *A61L 27/303* (2013.01); *A61L 27/306* (2013.01); *A61L 27/50* (2013.01); *A61L 29/103* (2013.01); *A61L 29/106* (2013.01); *A61L 29/14* (2013.01); *A61L 31/084* (2013.01); *A61L 31/088* (2013.01); *B23K 26/00* (2013.01); *C23C 24/04* (2013.01); *A61F 2/06* (2013.01); *A61L 2400/12* (2013.01); *A61L 2400/18* (2013.01); *A61L 2420/02* (2013.01)

(58) Field of Classification Search
CPC ............. A61F 2/06; A61M 31/00; B05D 1/04
USPC ............... 427/2.24, 2.28, 475, 481, 483, 485; 604/502; 623/1.15
See application file for complete search history.

(56) References Cited

U.S. PATENT DOCUMENTS 6,309,380 B1 * 10/2001 Larson ................. A61K 9/0024
128/898
6,803,070 B2 * 10/2004 Weber ................... A61L 27/446
427/2.24
2009/0118815 A1 * 5/2009 Arcand ................... A61L 31/08
623/1.15

FOREIGN PATENT DOCUMENTS

WO WO 2008/057710 5/2008
WO WO 2011/005165 1/2011
WO WO 2011/064392 6/2011

OTHER PUBLICATIONS

International Search Report and Written Opinion in International Application No. PCT/US2013/069696, mailed Jan. 30, 2014, 16 pages.

(Continued)

*Primary Examiner* — Andrew Bowman
(74) *Attorney, Agent, or Firm* — Seager, Tufte & Wickem, LLP

(57) ABSTRACT

Nanoparticles can be embedded into a medical device by accelerating them to a speed of between 100 m/s and 1,000 m/s and embedding the particles into a polymer surface of a medical device or a precursor thereof. In some cases, the nanoparticles can be embedded until the nanoparticles accumulate in sufficient number to adhere together to form a coating over the polymer surface. The nanoparticles can provide a conductive pathway, an abrasion resistant surface, a pro-healing surface, and/or an anti-bacterial surface.

16 Claims, 6 Drawing Sheets

(51) Int. Cl.
*A61L 29/14* (2006.01)
*A61L 31/08* (2006.01)
*A61L 27/30* (2006.01)
*A61L 27/50* (2006.01)
*C23C 24/04* (2006.01)
*B23K 26/00* (2014.01)
*A61F 2/06* (2013.01)

(56) References Cited

OTHER PUBLICATIONS

Bongiorno et al., "Nanostructured $CN_x$ ($0 < x < 0.2$) films grown by supersonic cluster beam deposition," *Carbon*, 2005, 43:1460-1469.

Corbelli, et al. "Highly Deformable Nanostructured Elastomeric Electrodes With Improving Conductivity Upon Cyclical Stretching," *Adv. Mater.*, 2011, 4504-4508.

Hu et al., "Thin-film nucleation through molecular cluster beam deposition: Comparison of tight-binding and many-body empirical potential molecular dynamics simulations," *J Chem Physics*, Apr. 15, 2002, 116(5):6738-6744.

Marelli et al., "Flexible and biocompatible microelectrode arrays fabricated by supersonic cluster beam deposition on SU-9," 16 pages.

Ostergard, "Polypropylene Vaginal Mesh Grafts in Gynecology," *Obstetrics & Gynecology*, Oct. 2010, 116(4):962-966.

Scopelliti et al., "The Effect of Surface Nanometre-Scale Morphology on Protein Adsorption," *PLoS One*, Jul. 2010, 5(7):e11862, 9 pages.

Wegner et al., "Cluster beam deposition: a tool for nanoscale science and technology," *J Phys D: Appl Phys*, 2006, 39:R439-R459.

\* cited by examiner

NANOPARTICLE IMPLANTATION IN MEDICAL DEVICES

TECHNICAL FIELD

This document relates to implanting nanoparticles into medical devices.

BACKGROUND

Dilatation catheters are devices that have an inflatable balloon at the distal end and are utilized in medical procedures such as angioplasty to eliminate stenoses or blockages. The balloons are inserted into vessels in the body to open stenoses or blockages in the vascular system, usually by means of a catheter having a balloon at its distal end. To this end, the catheters may be inserted into a blood vessel, advanced through the blood vessel to a target site (i.e. the location of the stenosis or blockage) and the balloon is then inflated by supplying a liquid such as a radiopaque substance for angiography, through an inflation lumen. The inflation of the balloon causes stretching and expansion of the target site, i.e. a blood vessel, in order to eliminate the stenosis or blockage, thereby reestablishing acceptable blood flow. There are various types of catheters having single or multiple lumens, some of which are over-the-wire and some of which are not.

Dilatation balloons are typically made of polymeric materials including nylon, polyether-polyester block copolymers, poly(amide-ether-ester) block copolymers, polyethylene terephthalate, polytetrafluoroethylene, polyvinyl chloride, polyurethanes, polyetherurethanes, polyesterurethanes, polyurethane ureas, polyurethane siloxane block copolymers, polyethylene, polypropylene or other similar extrudable thermoplastic, polymeric materials, or composites thereof. Polymeric films, however, can be damaged by abrasion and can puncture during use, especially when in the presence of calcified lesions. Polymeric balloon catheters can also be compromised during manufacturing. For example, pinholes can be formed during stent crimping.

Some balloon catheters are designed to supply a moderate amount of heat to a target site. Thermal energy is capable of denaturing the tissue and modulating the collagenous molecules in such a way that treated tissue becomes more resilient. Thermal energy can be supplied to a target site using a radiofrequency ablation catheter. Radiofrequency energy, when coupled with a temperature control mechanism, can be supplied precisely to the electrode-to-tissue contact site to obtain the desired temperature for treating a tissue. Radiofrequency ablation catheters, however, require a permeable membrane to conduct electrons from the coil in the center of the balloon through the thickness of the membrane and into the tissue. The holes in the membrane need to be small enough to ensure that the balloon does not burst, but still large enough to conduct. Some designs use layered structures having an inner permeable layer and an outer dielectric coating, leaving windows to act as electrodes.

Other medical devices include medical implants. In some cases, certain medical implants can be made of polymers or other materials having certain desired bulk material properties. Certain implant materials, however, can be prone to an inflammatory response and/or bacterial growth, which can cause clotting or other undesirable clinical outcomes. For example, medical implants can include heart valves, occlusions (e.g., left atrial appendage occlusions), vaginal meshes, stents, and stent grafts.

SUMMARY

This document describes nanoparticle implantation techniques for forming medical devices. In general, the methods provided herein include accelerating nanoparticles and embedding the particles into the surface of a medical device or a precursor thereof. The nanoparticles can be embedded until the nanoparticles accumulate in sufficient number to accumulate and adhere together at the surface. A coating formed on a surface can have a thickness such that the bulk properties of the underlying material do not significantly change. In some case, the nanoparticles can include metal and can be used to metallize a surface.

The plurality of nanoparticles, in some cases, can be accelerated to supersonic speeds. The plurality of nanoparticles can have enough momentum to embed in the material of the surface of the medical device. In some cases, the plurality of nanoparticles are accelerated to a speed of between 100 m/s and 1,000 m/s. A resulting coating can have a significantly higher adhesion that other coating methods For example, a coating can have a thickness of less than 1000 nm. In some cases, the nanoparticles are not positively or negatively charged during implantation. In some case, the nanoparticles have a temperature of less than 100° C. during implantation.

The surface of the medical device can include a polymer. In some cases, the polymer can include nylon, Selar®, polyether-polyester block copolymers (e.g. Hytrel® or Amitel®), poly(amide-ether-ester) block copolymers such as Pebax®, polyethylene terephthalate (PET), polytetrafluoroethylene, polyvinyl chloride, polyurethanes, polyetherurethanes, polyesterurethanes, polyurethane ureas, polyurethane siloxane block copolymers, polyethylene, polypropylene or other similar extrudable thermoplastic, polymeric materials, or composites thereof.

The nanoparticles can have diameters of 1000 nm or less. In some cases, the nanoparticles have diameters of between 10 nm and 500 nm.

The nanoparticles can include a variety of different materials. In some cases, the nanoparticles include a metal. The metal nanoparticles can be used to metallize a surface (e.g., a polymer surface). Suitable metals include platinum, iridium, titanium, tungsten, chromium, gold, silver, iron, magnesium, and alloys or other combinations thereof.

In some cases, the nanoparticles comprise a metal oxide, a metal nitride, a nitrate, an iodide, carbon nanotubes, or a combination thereof.

The medical device can be a device that is introduced into the body. In some cases, the medical device includes a dilatation balloon. In some cases, the dilatation balloon is a radiofrequency ablation balloon. For example, the methods provided herein can include forming one or more holes in a dilatation balloon and embedding the plurality of nanoparticles into one or more surfaces of the one or more holes in order to form a conductive pathway through the dilatation balloon and allow the dilatation balloon to be used as a radiofrequency ablation balloon. In some cases, the holes are filled thereafter.

In some cases, the medical device is a medical implant. For example, the medical implant can be a heart valve, a left atrial appendage occlusion device, a vaginal mesh, a stent, a graft, or a stent graft.

In some cases, the methods provided herein may provide a robust adhesion between a polymer and a metallized surface. For example, the embedded nanoparticles can accumulate in the material under the surface of a polymer medical device until the nanoparticles begin to impact other embedded nanoparticles with such momentum that the nanoparticles start to merge at the surface and form a metal layer. A mixture of polymer and metal under the surface metal layer are intermixed to form a strong connection. In some cases, the metal surface is flexible such that it does not alter the bulk mechanical properties of the polymer. The metal surface can provide an abrasion and/or puncture resistant layer, a pro-healing surface, and/or an anti-bacterial surface.

In some aspects, a method provided herein includes preparing a dilatation balloon by accelerating a plurality of nanoparticles to a speed of between 100 m/s and 1,000 m/s and embedding the accelerated nanoparticles into a polymer balloon wall to form a network of fused nanoparticles. The network of fused nanoparticles can form a conductive pathway between an inside surface of the polymer balloon wall and an outside surface of the polymer balloon wall. The method can include forming one or more holes in the polymer balloon wall and embedding the plurality of nanoparticles into at least one or more surfaces of the one or more holes to form the conductive pathway between the inside surface of the polymer balloon wall and the outside surface of the polymer balloon wall. In some cases, the method provided herein can include forming one or more holes in the polymer balloon wall and embedding the plurality of nanoparticles into at least one or more surfaces of the one or more holes and filling the hole with a material. The network of fused nanoparticles or the material filling the hole can form a conductive pathway through the thickness of the dilatation balloon. The nanoparticles can include a metal. The network of fused nanoparticles can form a continuous coating of fused nanoparticles over an outer surface of the polymer balloon wall.

In some aspects, a method provided herein includes forming a coating on a polymer surface by accelerating a plurality of nanoparticles to a speed of between 100 m/s and 1,000 m/s and embedding the accelerated nanoparticles into a polymer surface of a heart valve, a left atrial appendage occlusion device, a vaginal mesh, or a precursor thereof. The nanoparticles can be embedded until the embedded nanoparticles fuse together and a continuous coating of fused nanoparticles is formed over the polymer surface of the medical implant. The network of fused nanoparticles can form a conductive pathway on the polymer surface.

In some aspects, a method provided herein includes accelerating a plurality of nanoparticles including an anti-bacterial agent to a speed of between 100 m/s and 1,000 m/s and embedding the accelerated nanoparticles into a polymer surface of a heart valve, a left atrial appendage occlusion device, a vaginal mesh, or a precursor thereof. The anti-bacterial agent can include silver or a silver salt.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

This document describes nanoparticle implantation techniques for creating improved medical devices. The nanoparticle implantation techniques provided herein can be used to create strongly adherent surface coatings on a substrate surface. In some cases, the nanoparticles include a metal and the substrate surface includes a polymer such that the use of the nanoparticle implantation techniques provided herein can produce a polymeric medical device having a metallized surface coating. The surface coating can be flexible and allow the medical device to retain the bulk mechanical properties of the underlying structure.

Figure 1A:
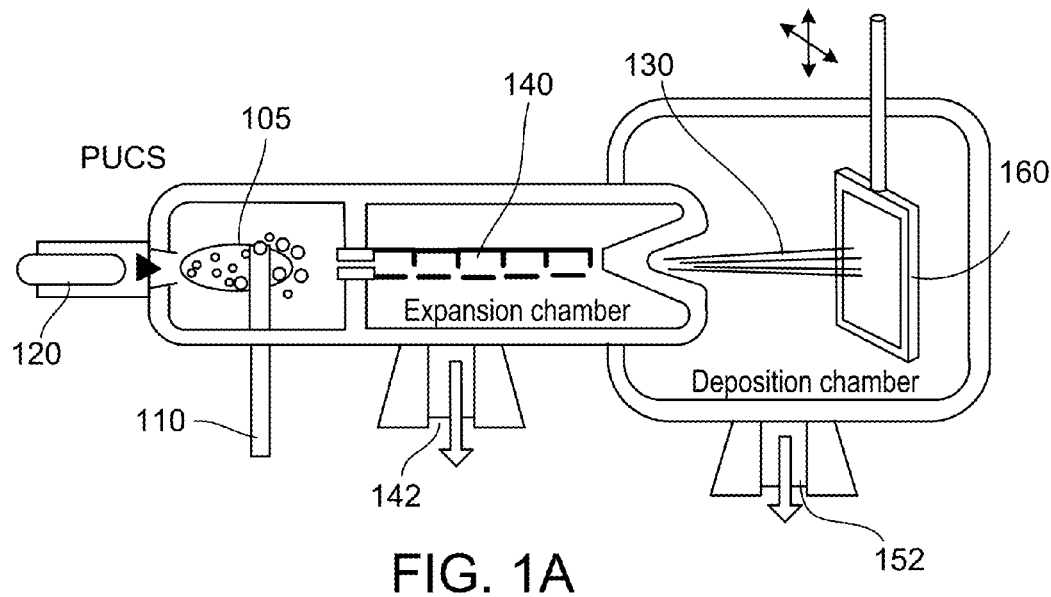
FIG. 1A-1B is a schematic illustrating a supersonic cluster beam deposition process.

The nanoparticle implantation techniques provided herein can include supersonic cluster beam deposition processes. FIG. 1 is a schematic illustrating a supersonic cluster beam deposition process. Supersonic cluster beam deposition can include generating nanoparticles using laser or sputtering techniques. FIG. 1a depicts a material source 110 that is introduced into a nanoparticle forming chamber 105 and a laser 120 forms the material source into nanoparticles 130. The nanoparticles 130 can be accelerated in an acceleration chamber 140. The acceleration chamber 140 can accelerate the nanoparticles 130 to supersonic speeds using high pressure gasses or through ultra-high vacuum systems. The acceleration chamber 140 can include a vent 142. Nanoparticles 130 traveling at supersonic speeds can then enter a deposition chamber 150 where they can impact a medical device 160 at supersonic speeds. The nanoparticles 130 can have enough momentum to embed themselves into one or more surfaces of the medical device 160. The deposition chamber 150 can also include a vent 152.

Figure 1B:
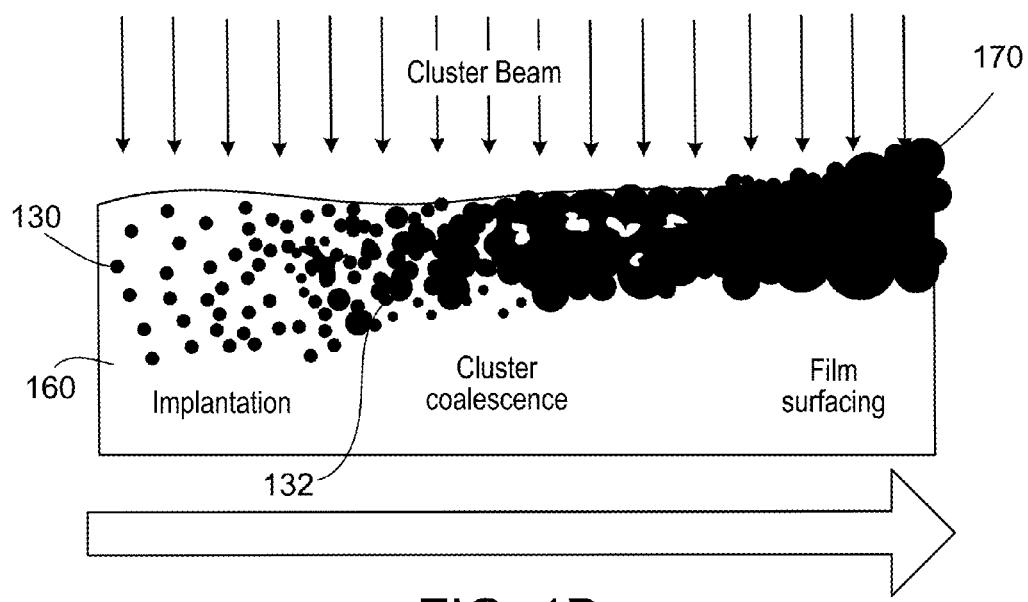

After sufficient nanoparticles 130 are embedded, nanoparticles begin to impact each other and bond, eventually forming a metal surface layer 170 on a surface of the medical device 160. As shown in FIG. 1b, the process begins with nanoparticles becoming embedded and dispersed within a substrate material (e.g., polymer). As more nanoparticles are embedded and impact each other, clusters 132 begin to form. As more nanoparticles 130 are embedded, the clusters begin to coalesce until a film 170 of the nanoparticle material forms on the medical device 160. In some cases, the film layer is metallic and the surface includes a polymer (e.g., PET).

Figures 2A, 2B, 2C:
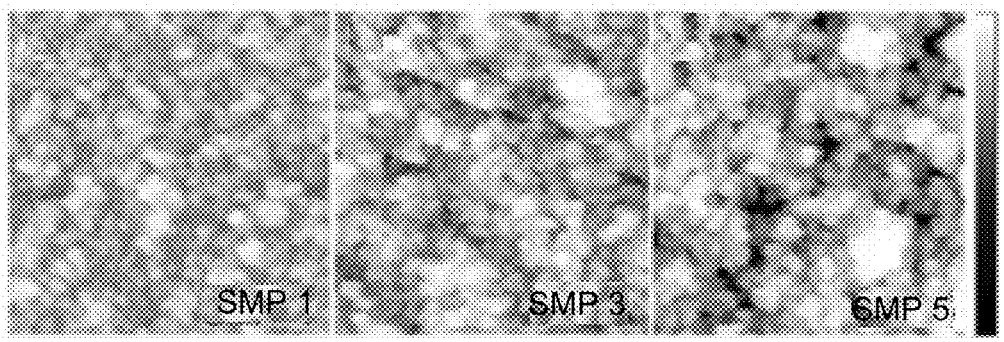
FIG. 2A-2D illustrates structures that can result from a supersonic cluster beam deposition.
Figure 2D:
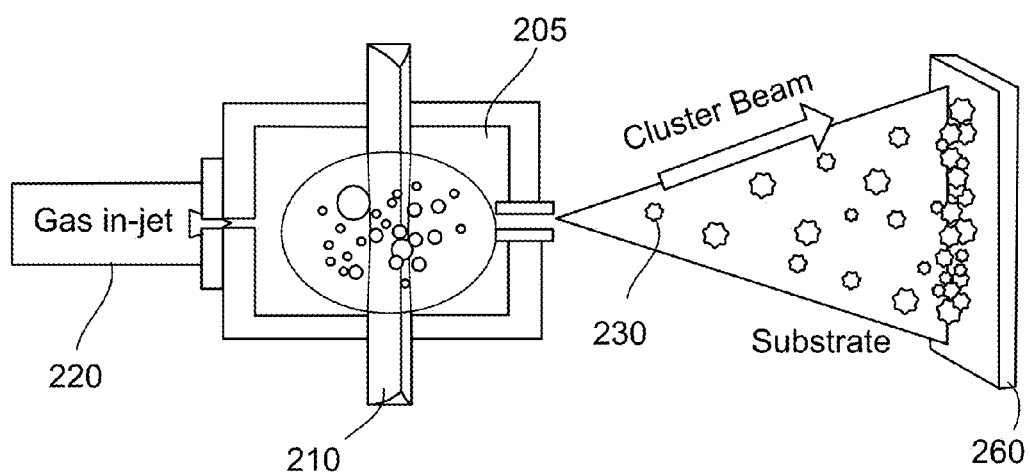

FIG. 2 illustrates structures that can result from a supersonic cluster beam deposition. FIGS. 2A-2D shows the progression of particle build up as the material is deposited into and on a substrate. As shown, the metal and polymer can actually be interspersed, which can result in a strong adherence between the embedded material (e.g., metal nanoparticles) and the substrate material (e.g., polymer). Other nanoparticle implantation techniques using accelerated nanoparticles are also contemplated. For example, FIG. 2 also depicts how a gas in-jet 220 can be used to accelerate nanoparticles 230 formed from a Pulsed Microplasma Cluster Source ("PMCS") 205 towards a medical device 260. The processes for depositing nanoparticles are also described in Corbelli, et al. "Highly Deformable Nanostructured Elastomeric Electrodes With Improving Conductivity Upon Cyclical Stretching, Adv. Mater. 2011, 4504-4508, the entire content of which is hereby incorporated by reference.

The methods provided herein can include accelerating particles to a speed of at least 100 m/s. In some cases, the particles can be accelerated to a speed of at least 150 m/s, at least 200 m/s, at least 250 m/s, at least 300 m/s, at least 310 m/s, at least 320 m/s, at least 330 m/s, at least 340 m/s, at least 350 m/s, or at least 400 m/s. In some cases, the particles are accelerated to a maximum speed of 1000 m/s. [In some cases, the particles can be accelerated to a maximum speed of 990 m/s or less, 975 m/s or less, 950 m/s or less, 900 m/s or less, 800 m/s or less, 700 m/s or less, 600 m/s or less, 500 m/s or less, 400 m/s or less, or 350 m/s or less. In some cases, the particles are accelerated to a maximum speed of 1000 m/s. In some cases, the particles can be accelerated to a speed of between 100 m/s and 1000 m/s, between 200 m/s and 800 m/s, between 340 m/s and 700 m/s, or between 400 m/s and 600 m/s.

The nanoparticles can be formed by any appropriate method. In some cases, the nanoparticles can be formed in a gas phase by either homogeneous nucleation or by coagulation (collision) processes. For example, a starting material can be vaporized into a low density inert gas using Joule heating, thermal plasma, or laser ablation. Rapid cooling of the vapor can result in supersaturation followed by homogeneous nucleation and the formation of nanoparticles.

In some cases, the nanoparticles impact the surface of the medical device at a temperature of less than 100° C. In some cases, the nanoparticles impact the surface of the medical device at a temperature of less than 80° C., less than 60° C., or less than 40° C. In some cases, the nanoparticles are not positively or negatively charged when they impact the surface of the medical device.

As used herein, the term "nanoparticle" means a particle having a diameter of between 1 nm and 1000 nm. In some cases, the nanoparticles used in the methods provided herein can have an average diameter of 950 nm or less, 900 nm or less, 750 nm or less, 500 nm or less, 250 nm or less, or 100 nm or less. In some cases, the particles have an average diameter of between 2 nm and 1000 nm, between 10 nm and 500 nm, between 100 nm and 250 nm, between 100 nm and 1000 nm, between 500 nm and 1000 nm, or between 100 nm and 500 nm.

The surface of the medical device can include any appropriate material. In some cases, the surface of the medical device includes a polymer. In some cases, the polymer can include nylon, Selar®, polyether-polyester block copolymers (e.g. Hytrel® or Amitel®), poly(amide-ether-ester) block copolymers such as Pebax®, polyethylene terephthalate (PET), polytetrafluoroethylene, polyvinyl chloride, polyurethanes, polyetherurethanes, polyesterurethanes, polyurethane ureas, polyurethane siloxane block copolymers, polyethylene, polypropylene or other similar extrudable thermoplastic, polymeric materials, or composites thereof.

The nanoparticles can include any appropriate material. In some cases, the nanoparticles include a metal. The metal nanoparticles can be used to metallize a surface (e.g., a polymer surface) to improve abrasion resistance, provide an antibacterial surface, provide a biocompatible surface, and/or provide a conductive surface to the medical device. In some cases, metal nanoparticles can be embedded in a medical device surface to provide a conductive path thorough a portion of the medical device (e.g., to provide a conducitive path through a dilatation balloon). For example, metal nanoparticles can include platinum, iridium, titanium, tungsten, chromium, iron, magnesium, silver, gold, or any alloy or combination thereof.

In some cases, the nanoparticles can include a ceramic. In some cases, the nanoparticles can include a metal oxide (e.g., $TiO_x$, $CrO_x$, or $IrO_x$). For example, a $TiO_x$ and/or $CrO_x$ surface layer can provide a highly biocompatible surface that absorbs and adheres to proteins found in a physiological environment. In some cases, a pattern of metal oxides could be deposited to provide a desired pro-healing surface of a medical device. For example, specific areas of a medical implant could be treated to modify cell growth and/or adhesion along certain parts of the implant.

In some cases, the nanoparticles can include a metal nitride or metal nitrate (e.g., magnesium nitride or silver nitrate). In some cases, the nanoparticles can include fullerenes (e.g., carbon nanotubes and/or buckyballs). In some cases, the nanoparticles can include silver or a silver salt (e.g., silver nitrate, silver sulfadiazine, or silver iodide), which can impart antibacterial properties to the medical device.

Figure 3:
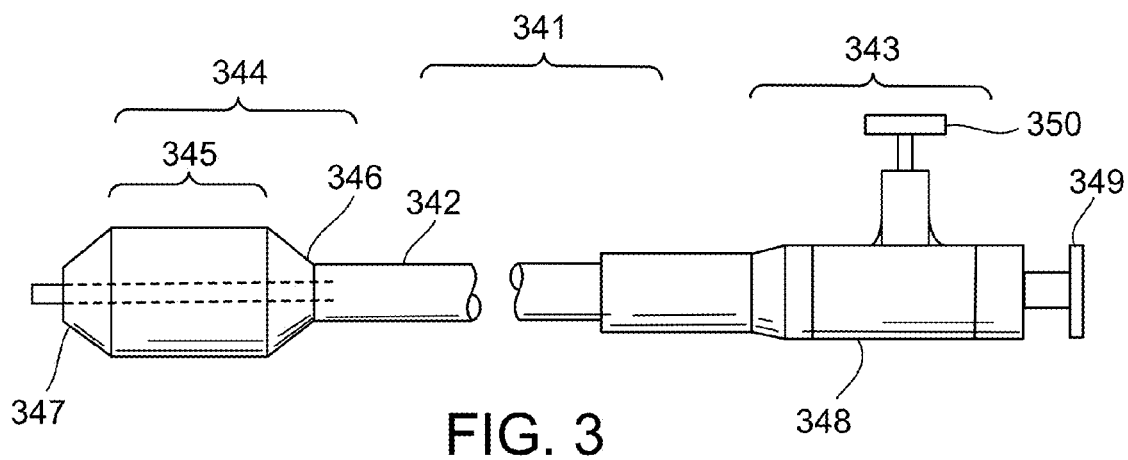
FIG. 3 is a schematic view of a of a dilatation balloon catheter.

FIG. 3 is a perspective view of an exemplary dilatation balloon catheter 341. The catheter 341 can include additional features known in the vascular dilatation art, such as implantable stents, drug delivery, perfusion and dilatation features, or any combination of these features. The catheter 341 includes an elongate flexible tubular body 342 extending between a proximal control end 343 and a distal functional end 344. In some cases, a portion or all of the length of tubular body 42 may include a spring coil, solid walled hypodermic needle tubing, braided reinforced wall tubing, or the like. The tubular body 342 can have a generally circular cross-sectional configuration having an external diameter in the range from about 0.05 cm to about 0.3 cm. The tubular body 342 can have a length in the range of 20 cm to 150 cm. In some cases, the tubular body 342 can have a generally triangular, oval or double-circular cross-sectional configurations, as well as other noncircular configurations depending upon the intended use. The tubular body 342 can have sufficient structural integrity to permit the catheter to be advanced to distal arterial locations without buckling or undesirable bending of the tubular body 342. In some cases, the tubular body 342 can be adapted to transmit torque to the distal functional end 344.

As illustrated in FIG. 3, a distal functional end 344 is provided with an inflatable balloon 345 having a proximal end 346 and a distal end 347. In some cases, the inflatable balloon 345 can be conductive and be adapted for radiofrequency ablation. The proximal control end 343 of catheter 341 can be provided with a manifold 348 having a plurality of access ports. The manifold 348 can be provided with a guidewire port 349 in an over the wire embodiment and a balloon inflation port 350. The balloon 345 can also be mounted on a rapid exchange type catheter.

Figure 4:
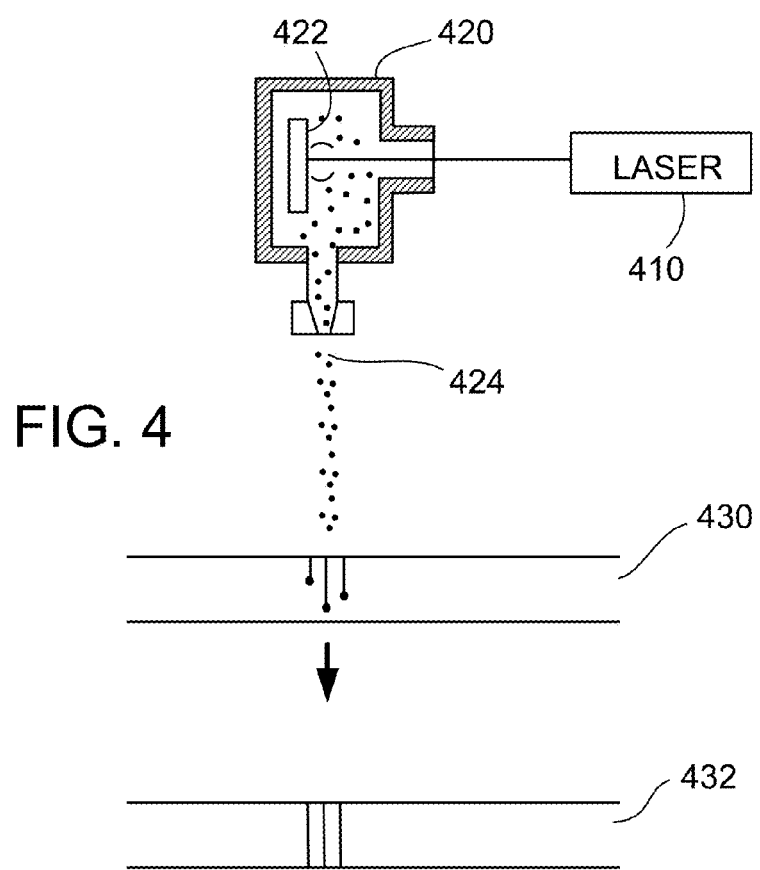
FIG. 4 is an illustration of how nanoparticles can become embedded in a surface using methods provided herein.

FIG. 4 is an illustration of how nanoparticles can become embedded in a surface of a medical device using methods provided herein. In some cases, the surface 430 can be the balloon of a dilatation balloon, such as that shown in FIG. 3. Nanoparticles can be embedded and possibly pass entirely through the thickness of a dilatation balloon wall. For example, radiofrequency ablation balloon catheters need a balloon that can conduct electrons from an internal coil in the center of the balloon though the balloon wall and into the tissue. This can be achieved by having a conductive material for the balloon, but conductive materials may not have other material properties optimal for use as a balloon material. This can also be achieved by having small holes in the balloon wall, but these holes should be sized to allow conductivity through the balloon wall but small enough to preserve the burst strength of the balloon material. FIG. 4 depicts a method provided herein where nanoparticles 424 are formed in a chamber 420 from a source material 422 using a laser 410 and accelerated towards a balloon wall surface 430 to create permeability/conductivity. Nanoparticles 424 can pass all the way through the surface of the balloon wall 430 to create pores having dimensions of less than 10 microns and/or become embedded in the balloon wall surface 430 to provide conductivity through the thickness of the balloon wall 430.

For example, after sufficient nanoparticles 424 are embedded, embedded nanoparticles can form a conductive network through the thickness of the balloon wall. A balloon wall 432 having a conductive network there through can also have porosity resulting from nanoparticles 424 passing through the balloon wall.

Figure 5:
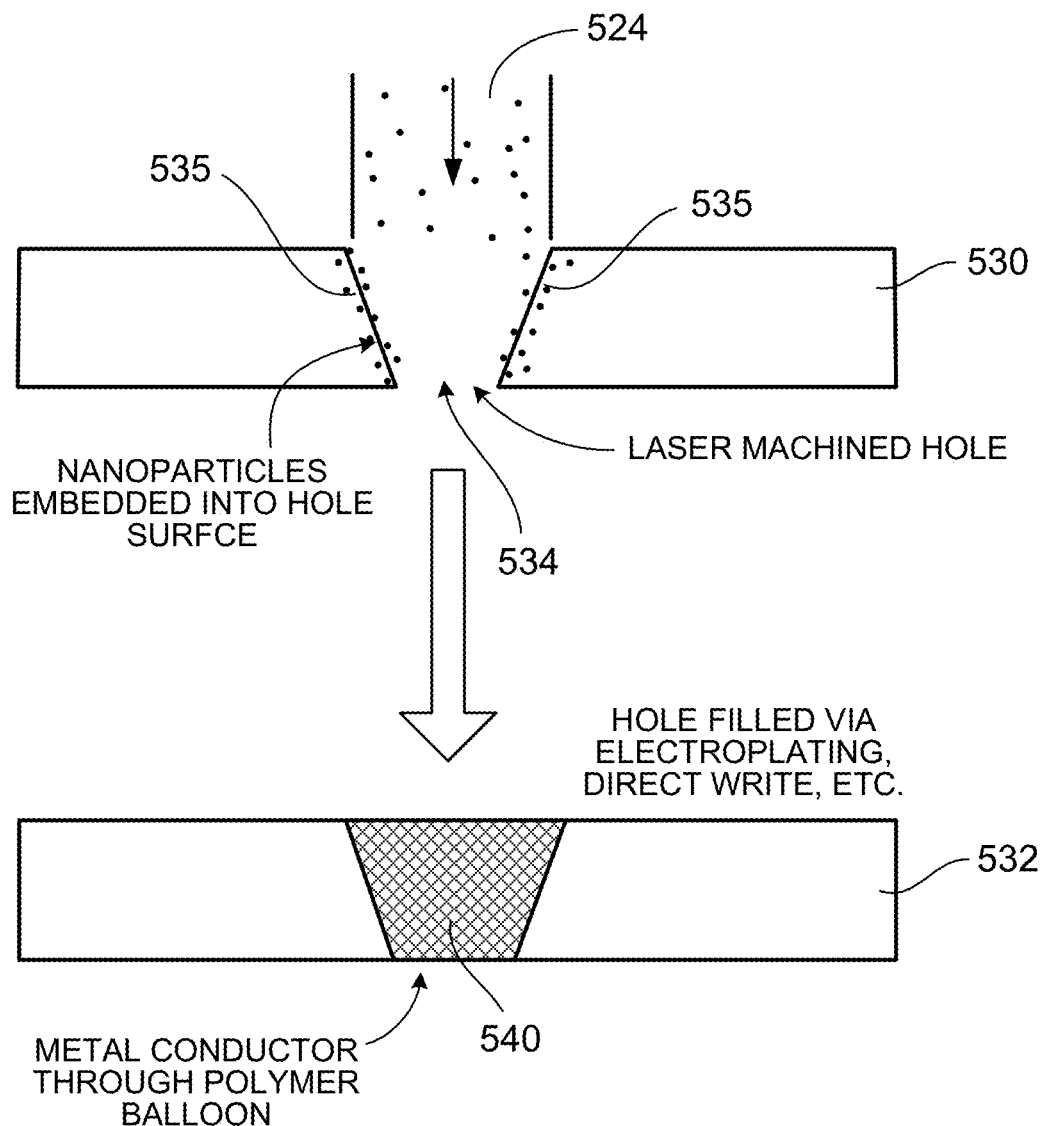
FIG. 5 is an illustration of how a conductive path can be formed though the thickness of a dilatation balloon using a method provided herein.

FIG. 5 is an illustration of how a conductive path can be formed though the thickness of a dilatation balloon wall 530 using a method provided herein. In some cases, holes 534 can be formed in a dilatation balloon 530 and then filled in with a material 540 to form a conductive dilatation balloon wall 532. One or more holes 534 can be formed by laser, by machine, or by any other appropriate method. The hole can be filled in by first accelerating nanoparticles and embedding the nanoparticles into a surface 535 of the hole 534 until the nanoparticles coalesce and form a network or film along the inside surface 535 of the hole 534. The hole 534 can then be filled using electroplating, direct write printing, or any other appropriate technique. In some cases, nanoparticles 524 are deposited until the hole 534 is filled with fused nanoparticles. The nanoparticle 524 and/or the material 540 used to fill the bulk of the hole 534 can be conductive to provide a conductive pathway through the thickness of the dilatation balloon wall 532. The embedded nanoparticles can have good adhesion to the dilatation balloon wall 532, and can also have good adhesion to the material 540 used to completely fill in the hole (e.g., either because of material compatibility and/or because of a suitable surface roughness of the network or film of nanoparticles formed on the inside surface of the hole).

Figure 6:
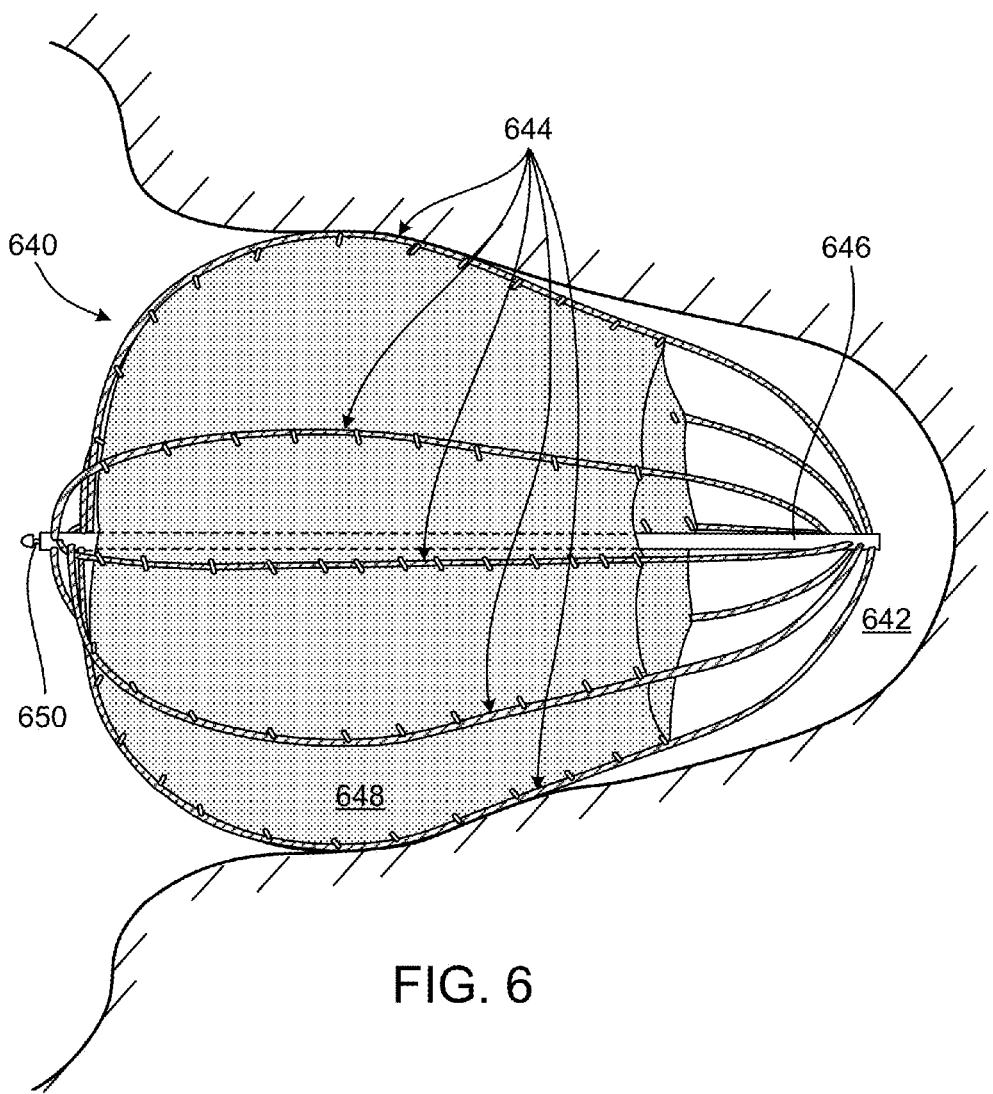
FIG. 6 is a perspective view of a left atrial appendage occlusion device.

FIG. 6 is a perspective view of a left atrial appendage ("LAA") occlusion device 640 deployed within the LAA 642. The LAA is a small cavity that is thumb-like in shape and is located off the left atrium. The occlusion device 640 can include a plurality of ribs 644, a center post 646, a sheet 648, and a grasping knob 650. To secure the occlusion device 640 in the LAA 642, the ribs 644 exert a radial force which presses outwards against the walls of the LAA 642. Although the shape of the device 640 may vary somewhat, the device 640 can be shaped to fit in the LAA 642 so that it remains securely deployed and prevents blood from entering or exiting the LAA 642. Once the device 640 is deployed, the cavity of the LAA 642 is occluded and thus, new thrombi cannot form in the LAA 642. Further, because the LAA 642 is occluded, existing thrombi cannot exit the LAA 642. Because thrombi cannot form in the LAA 642 and existing thrombi cannot exit the LAA 642, the occlusion device 640 helps to minimize the incidence of stroke. Sheet 648 can have an outer film formed by embedding nanoparticles into the sheet 648. The film can improve the puncture and abrasion resistance of the sheet 648, which can ensure that existing thrombi cannot exit the LAA 642. In some cases, a patterned film formed by embedding nanoparticles can control cell growth into and/or around certain sections of the LAA 642.

Figure 7:
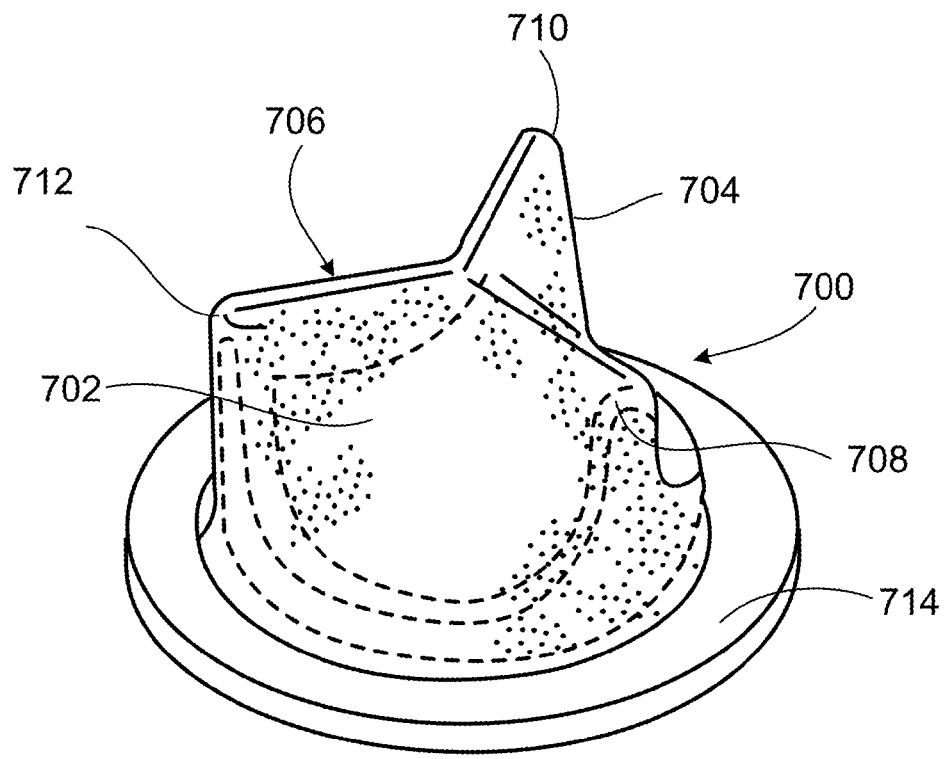
FIG. 7 is a perspective view of a heart valve.

FIG. 7 is a perspective view of a heart valve prosthesis 700 with flexible polymer leaflets or occluders. Heart valve prosthesis 700 includes leaflets 702, 704, 706 joined at commissures 708, 710, 712, and sewing ring 714. Sewing ring 714 can be used to attach valve 700 to patient tissue with sutures, adhesives or other attachment mechanisms. Although shown with three polymer leaflets, the prostheses can be constructed with different numbers of polymer leaflets, such as two leaflets.

Leaflets 702 can include a flexible polymer having a film formed thereon by embedding nanoparticles into the leaflets 702 by a process provided herein. The film can improve the puncture and abrasion resistance of the leaflets 702. The film can also improve the durability of the leaflets 702 to withstand the repeated cycling required for replacement heart valve use.

Figure 8:
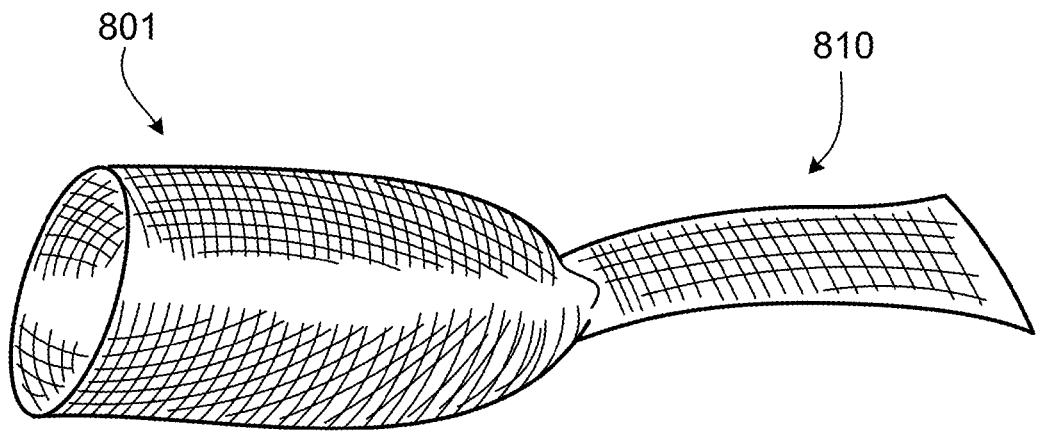
FIG. 8 is a perspective view of a vaginal mesh.

FIG. 8 is a perspective view of an exemplary tubular vaginal mesh 800 for sacrocolpopexy. Other mesh materials for other reconstructive surgeries are also contemplated. The tubular vaginal mesh 800 can have a conical structure 801 to surround the entire circumference of the vaginal vault, which may be altered by the surgeon by cutting some mesh out. The tubular vaginal mesh can have an extension 810 that extends to the sacrum for apical suspension. The tubular vaginal mesh 800 can include one or more of several polymeric materials having nanoparticles embedded therein as provided herein. For example, the mesh can include macroporous, monofilament polypropylene having embedded nanoparticles. The vaginal mesh can have some elasticity so that it may conform to the outer topography of the patient's vaginal vault.

A number of embodiments of different medical devices have been described. Nevertheless, it will be understood that the nanoparticle embedding techniques provided herein can be used on other types of medical devices. Moreover, various modifications may be made to the method provided herein without departing from the spirit and scope of the claims presented below. Accordingly, other embodiments are within the scope of the following claims.

What is claimed is:

1. A method of making a medical device or a precursor thereof having a polymer surface, comprising:
    (a) accelerating a plurality of nanoparticles to a speed of between 100 m/s and 1,000 m/s; and
    (b) embedding the accelerated nanoparticles into a polymer surface of a medical device or a precursor thereof; and
    wherein medical device or precursor thereof is a dilatation balloon or precursor thereof, further comprising forming one or more holes in a dilatation balloon and embedding the plurality of nanoparticles into at least one or more surfaces of the one or more holes, further comprising filling the hole with a material, wherein the plurality of nanoparticles or the material filling the hole forms a conductive pathway through the thickness of the dilatation balloon.

2. The method of claim 1, wherein the plurality of nanoparticles are accelerated to a speed of at least 340 m/s.

3. The method of claim 1, wherein the plurality of nanoparticles have a temperature of less than 100° C. when embedded into the polymer surface of the medical device or the precursor thereof.

4. The method of claim 1, wherein the plurality of nanoparticles are not positively or negatively charged when embedded into the surface of the medical device or the precursor thereof.

5. The method of claim 1, wherein the polymer surface of the medical device comprises nylon, polyether-polyester block copolymers, poly(amide-ether- ester) block copolymers, polyethylene terephthalate, polytetrafluoroethylene, polyvinyl chloride, polyurethanes, polyetherurethanes, polyesterurethanes, polyurethane ureas, polyurethane siloxane block copolymers, polyethylene, polypropylene, or a combination thereof.

6. The method of claim 5, wherein the polymer comprises polyethylene terephthalate.

7. The method of claim 1, wherein accelerated nanoparticles are embedded until a continuous coating of fused nanoparticles is formed over the polymer surface of the medical device or the precursor thereof.

8. The method of claim 7, further comprising depositing another material over the coating.

9. The method of claim 7, wherein the coating has a thickness of less than 1000 nm.

10. The method of claim 1, wherein the nanoparticles have diameters of between 10 nm and 500 nm.

11. The method of claim 1, wherein the nanoparticles comprise platinum, iridium, silver, gold, chromium, iron, magnesium, or a combination thereof.

12. The method of claim 1, wherein the nanoparticles comprise a metal oxide, a metal nitride, a nitrate, an iodide, a carbon nano tube, or a combination thereof.

13. A method of making a dilatation balloon, comprising:
 (a) accelerating a plurality of nanoparticles to a speed of between 100 m/s and 1,000 m/s; and
 (b) embedding the accelerated nanoparticles into a polymer balloon wall to form a network of fused nanoparticles; and
 wherein the network of fused nanoparticles form a conductive pathway between an inside surface of the polymer balloon wall and an outside surface of the polymer balloon wall, further comprising forming one or more holes in the polymer balloon wall and embedding the plurality of nanoparticles into at least one or more surfaces of the one or more holes to form the conductive pathway between the inside surface of the polymer balloon wall and the outside surface of the polymer balloon wall.

14. A method of making a dilatation balloon, comprising:
 (a) accelerating a plurality of nanoparticles to a speed of between 100 m/s and 1,000 m/s; and
 (b) embedding the accelerated nanoparticles into a polymer balloon wall to form a network of fused nanoparticles;
 further comprising:
 (c) forming one or more holes in the polymer balloon wall and embedding the plurality of nanoparticles into at least one or more surfaces of the one or more holes; and
 (d) filling the hole with a material, wherein the network of fused nanoparticles or the material filling the hole forms a conductive pathway through the thickness of the dilatation balloon.

15. The method of claim 13, wherein the nanoparticles comprise a metal.

16. The method of claim 13, wherein the network of fused nanoparticles form a continuous coating of fused nanoparticles over an outer surface of the polymer balloon wall.

* * * * *